United States Patent
Tuunanen

Patent Number: 6,040,192
Date of Patent: Mar. 21, 2000

[54] METHOD AND MEANS FOR MAGNETIC PARTICLE SPECIFIC BINDING ASSAY

[75] Inventor: Jukka Tuunanen, Helsinki, Finland

[73] Assignee: Labsystems Oy, Helsinki, Finland

[21] Appl. No.: 08/920,094

[22] Filed: Aug. 26, 1997

Related U.S. Application Data

[63] Continuation of application No. 08/495,514, filed as application No. PCT/FI94/00048, Feb. 1, 1994, abandoned.

[30] Foreign Application Priority Data

Feb. 1, 1993 [FI] Finland .................................. 930440
Jun. 21, 1993 [FI] Finland .................................. 932866

[51] Int. Cl.$^7$ .................................................. G01N 33/553
[52] U.S. Cl. .................. 436/177; 209/217; 209/225; 210/222; 210/695; 422/65; 422/101; 435/287.2; 435/287.3; 435/287.9; 436/526; 436/806; 436/808
[58] Field of Search ........................... 436/526, 806, 436/808, 177; 422/101, 65; 210/222, 695; 209/212, 213, 214, 215, 217, 225; 435/287.1, 287.2, 287.3, 287.9

[56] References Cited

U.S. PATENT DOCUMENTS

| | | | |
|---|---|---|---|
| 2,471,764 | 5/1949 | Miller et al. | 294/65.5 |
| 3,904,482 | 9/1975 | Mehl | 195/109 |
| 3,970,518 | 7/1976 | Giaever | 436/526 |
| 3,985,649 | 10/1976 | Eddelman | 35/6 |
| 4,018,886 | 4/1977 | Giaever | 436/526 |
| 4,115,535 | 9/1978 | Giaever | 436/526 |
| 4,200,613 | 4/1980 | Alfrey et al. | 422/71 |
| 4,272,510 | 6/1981 | Smith et al. | 436/526 |
| 4,438,068 | 3/1984 | Forrest | 436/526 |
| 4,495,151 | 1/1985 | Ohyama et al. | 422/102 |
| 4,649,116 | 3/1987 | Daty et al. | 435/287 |
| 4,731,337 | 3/1988 | Luotola et al. | 436/526 |
| 4,751,053 | 6/1988 | Dodin et al. | 422/101 |
| 4,891,321 | 1/1990 | Hubscher | 435/293 |
| 4,895,650 | 1/1990 | Wang | 210/222 |
| 5,167,926 | 12/1992 | Kimura et al. | 422/67 |
| 5,200,084 | 4/1993 | Liberti et al. | 210/695 |
| 5,318,914 | 6/1994 | Matte et al. | 436/526 |
| 5,466,574 | 11/1995 | Liberti et al. | 435/5 |
| 5,474,742 | 12/1995 | Tuuminen | 422/63 |
| 5,647,994 | 7/1997 | Tuunanen et al. | 210/695 |

FOREIGN PATENT DOCUMENTS

| | | |
|---|---|---|
| 0 027 008 A1 | 4/1981 | European Pat. Off. . |
| 0 042 755 A3 | 12/1981 | European Pat. Off. . |
| 0186001 | 7/1986 | European Pat. Off. . |
| 0317286 | 5/1989 | European Pat. Off. . |
| 0351857 | 1/1990 | European Pat. Off. . |
| 0358948 | 3/1990 | European Pat. Off. . |
| 0479448 | 4/1992 | European Pat. Off. . |
| 0522322 | 1/1993 | European Pat. Off. . |
| 2824742 A1 | 2/1979 | Germany . |
| 58-5656 | 1/1983 | Japan . |
| 58-5657 | 1/1983 | Japan . |
| 58-5658 | 1/1983 | Japan . |
| 63-5263 | 1/1988 | Japan . |
| 63-5265 | 1/1988 | Japan . |
| 63-5266 | 1/1988 | Japan . |
| 1414479 | 11/1975 | United Kingdom . |
| 2147898 | 10/1984 | United Kingdom . |
| 2147 698 | 5/1985 | United Kingdom . |
| 86/06493 | 11/1986 | WIPO . |
| 87/05536 | 9/1987 | WIPO . |
| WO 9418564 | 8/1994 | WIPO . |
| WO 9418565 | 8/1994 | WIPO . |
| WO 9500247 | 1/1995 | WIPO . |
| WO 9612958 | 5/1996 | WIPO . |
| WO 9612959 | 5/1996 | WIPO . |
| WO 9612960 | 5/1996 | WIPO . |
| WO 9612961 | 5/1996 | WIPO . |

*Primary Examiner*—Jan Ludlow
*Attorney, Agent, or Firm*—Fish & Richardson P.C.

[57] ABSTRACT

A system and method for handling magnetic particles, as in an immunoassay. A remover having a magnetic body and covering sleeve is inserted in a vessel containing magnetic particles and a liquid. The remover is moved up and down with the particles adhered to agitate the liquid and improve adherence of the particles.

21 Claims, 3 Drawing Sheets

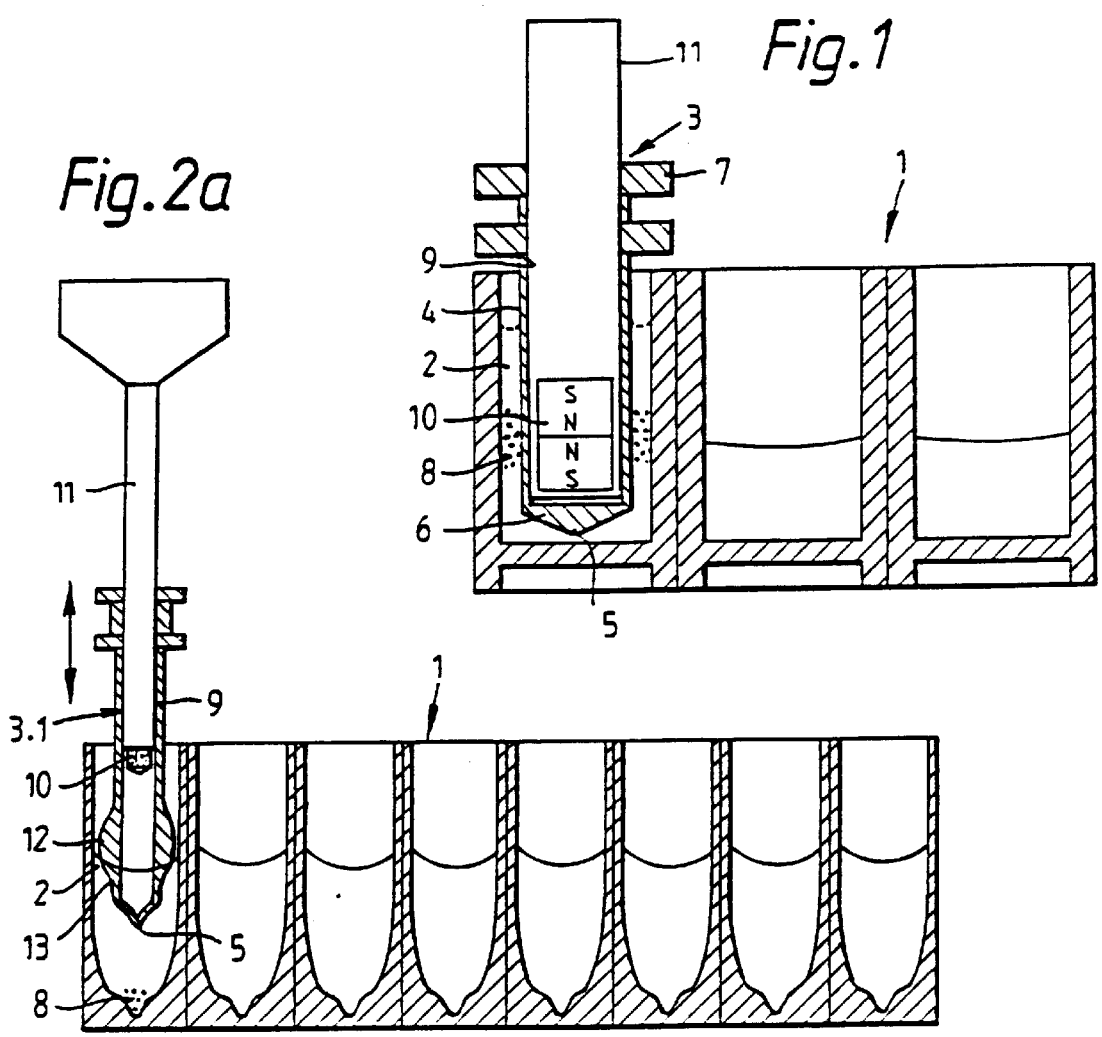
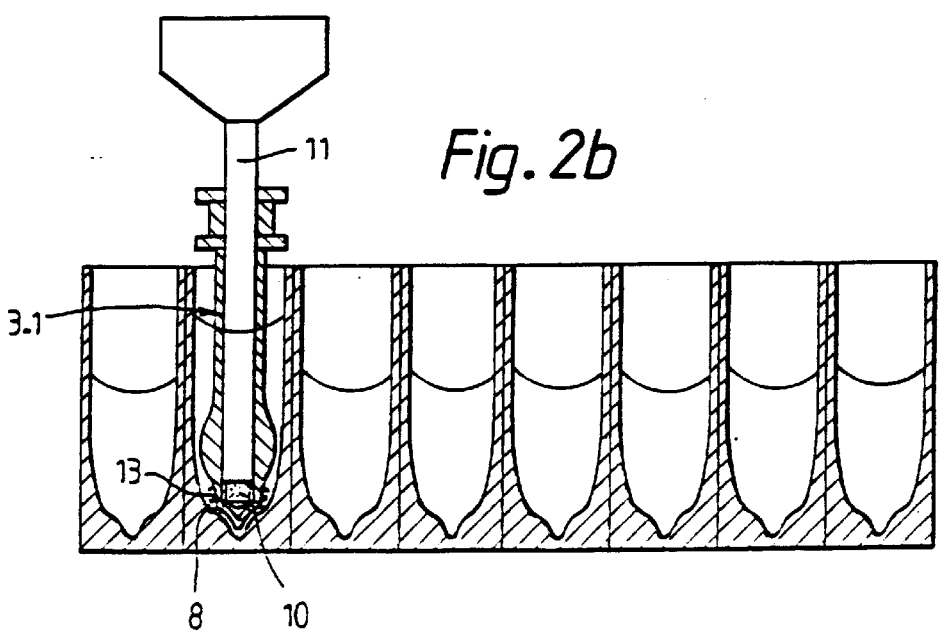

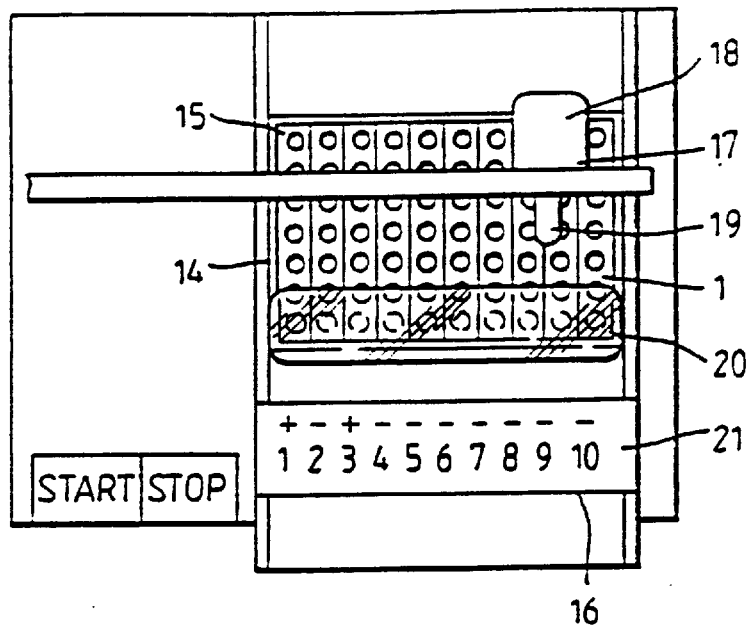
Fig.3
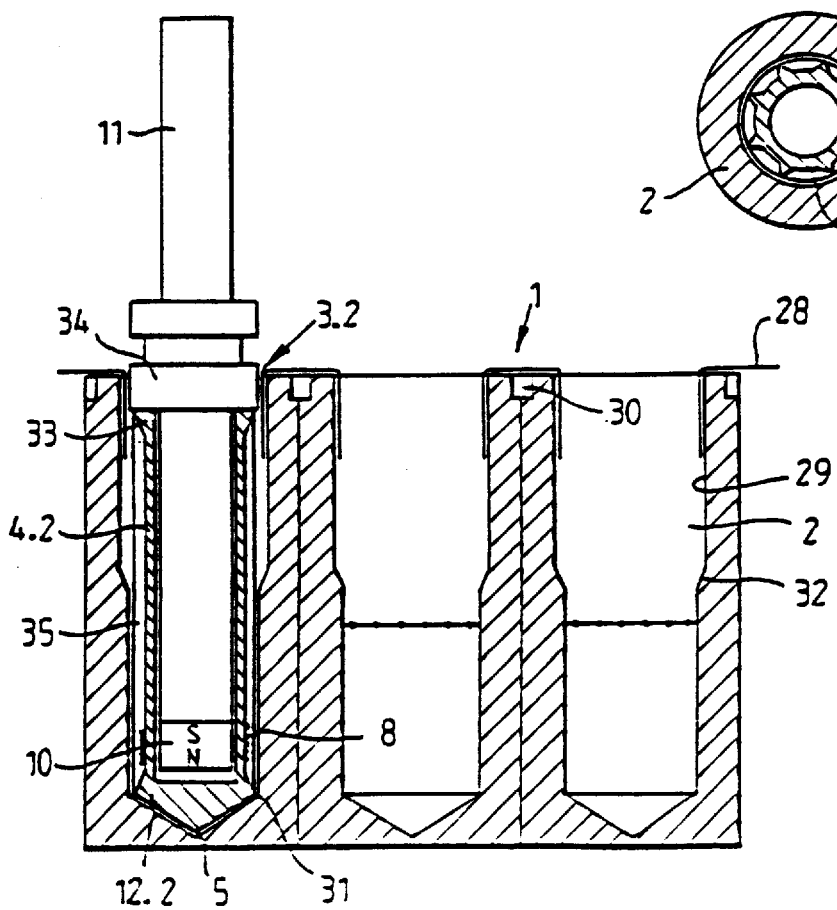
Fig.5
Fig.6

METHOD AND MEANS FOR MAGNETIC PARTICLE SPECIFIC BINDING ASSAY

This is a continuation of application Ser. No. 08/495,514, filed Jul. 28, 1995 now abandoned, which is a 371 of PCT/FI94/00048.

TECHNICAL FIELD

The invention concerns a determination method and equipment as well as an adapter for use in these. The invention is especially applicable to automatic immunodetermination systems.

TECHNICAL BACKGROUND

Solid-phase immunodetermination is usually performed in one vessel so that the analyte to be determined and possibly contained in the sample is first allowed to react with a separating reagent bound in a solid phase, whereupon the other steps required in the determination are performed in the same vessel. The troublesome thing here is that much dosing and removing of liquids must be performed. When several different determinations are done, a large stock of different reagents is also needed.

A system is also known wherein the solution to be used in each determination step is placed in advance in its own vessel. The solid phase is formed by the inside surface of a disposable pipette jet. In each step the pipette jet is brought into the respective vessel, the solution is drawn into the jet and a reaction is allowed to take place, whereafter the jet is emptied and moved into the next vessel. During the step of solution is moved back and forth in the jet. The equipment has several suction cylinders with pumps so that several determinations can be performed in parallel. No exact dosing devices are required in this equipment. Nor are any reagent containers required in the equipment. However, the drawback is that through a vapour phase samples are in connection with the cylinders of the equipment which can not, however, be washed automatically. This can cause a risk of contamination. Liquid will also remain in the pipette jet and will move along to the following step. In addition, piston pumps wear easily and unpredicatably, for which reason their condition must be checked often. Another problem is the sealing of the pipette jet to the suction cylinder. All things considered, much trouble can occur in this device. Besides, there is only limited solid-phase surface area available on the inner surface of the pipette jet.

DESCRIPTION OF THE INVENTION

A method of determination as defined in claim 1 has now been invented. Advantageous applications of the same are presented in the other claims.

As used herein, a separating reagent means such a substance which reacts with the analyte to be determined and binds it in a solid phase. In immunodeterminations the separating reagent is usually an antigen or an antibody. A medium here generally means a solution, such as a reaction solution or a washing fluid, to be used in some determination step.

The outer surface of solid particles separate from the reaction vessel is used as the solid phase in the method and the determination steps are carried out in two or several vessels. The particles are moved from one vessel to another using a special remover. The particles are kept in the vessel containing the sample and a separating reaction is allowed to take place. Then any other required steps are performed in other vessels, and finally the particles are moved to the measuring vessel. Mediums needed for the determination are dosed beforehand into the vessels.

The particles are preferably magnetic particles, whereby the remover preferably contains a magnet which can be moved in relation to the remover.

The vessels are preferably formed as one unit. In principle, however, some steps, especially measuring of the formed reaction product, can be performed outside the vessel unit, if desired. An outside measuring vessel could be used especially when the complex is detected directly from the solid phase, for example, fluorometrically or radiometrically.

Correspondingly, several steps, e.g. washes, can also be performed in the same vessel. A medium can also be dosed into some vessel or removed from it. Separate dosings could possibly be used in those steps where exact dosing is not necessary and where, for example, the same medium is used in several different determinations. Washes, in particular, could be such steps. However, normally such vessel units are more advantageous where all different medium are ready in different vessels.

At least washes are usually performed in intermediate determination steps. In addition, the resulting reaction complex is usually joined in a middle step to a tracer which is then detected in the measuring step. The tracer can be either directly detectable or it can be a tracer which releases a detectable compound from a special substrate. Detection usually takes place fluorometrically, luminometrically, absorptiometrically or radiometrically.

There is no risk of contamination in the method, because the sample is not drawn into the equipment from the plate vessels. In addition, the method can be carried out using simple and very reliably-operating automatic equipment.

The invention is suitable, for example, for immunologic, DNA-hybridization or hormone determinations.

The remover surface is preferably such that liquid will run off it as completely as possible. Preferably there is also a tip at the bottom end. The bottom of the reaction vessel is advantageously designed with the same shape as the remover, whereby as little medium as possible will be needed.

A very large solid-phase surface area is obtained by using solid-phase particles which are separate from the remover. The most advantageous ones are so-called microparticles. Magnetic particles are preferably used which are made to adhere easily to the remover with the aid of a magnet.

When using non-magnetic separate particles, the remover is provided, for example, with a grid or a filter to separate the particles from the medium.

To speed up mass transfer and thus also the necessary reaction time, the medium is preferably agitated during the reaction. This is preferably done by moving the remover. It is especially advantageous to move the remover in a vertical direction, whereby the medium must flow through a gap between the vessel and the remover, thus blending very effectively. To make blending more effective the remover is made so wide that a gap of a suitable narrowness is formed between the vessel and the remover. Agitation can also be promoted by a suitable remover and vessel design.

The vessel unit forms a plate for use in one determination. The remover can be packed into some vessel in the plate. The vessels for use in different steps may also be of different sizes.

The vessels are preferably closed with a film, which is punctured while carrying out the method. The film can be punctured by using the remover, but a separate puncturing point may also be used. The point may have cutting blades which form strips which tear in a controlled manner. The puncturing point may be attached to the same actuator as the remover in the equipment. The top edge of the vessel preferably has an extension against which the strips of the punctured film can rest. Closed vessels may contain an inert vapour phase to improve durability.

The equipment can also have a safeguarding system, which will make sure before the step is started that the vessel contains a medium. The remover may work conveniently as the indicator of such a system based on electric conductivity measurement.

If desired, in that reaction vessel in particular into which the sample is brought some suitable substance may be fastened to the vessel wall or to a separate solid phase remaining in the vessel, which substance binds such substances from the sample or from the formed complex which may disturb later determination steps.

The plate vessels are preferably in a single straight row, whereby the remover need be moved only along a straight path in the horizontal plane in relation to the plate. The vessels for the different steps may be located in any order in relation to each other. The vessels are preferably permanently fixed to one another. The plate may be made of some suitable material, preferably of plastic.

The plate is advantageously provided with detents and the equipment provided with their counterparts, so that the plate can not be located in a wrong position by mistake.

BRIEF DESCRIPTION OF THE DRAWINGS

Some applications of the invention will be described in the following by way of example. In the drawings of the description FIG. 1 shows a magnetic particle remover in a reaction vessel for use in implementation of the method, FIGS. 2a and 2b show implementation of the method by using magnetic particles and another remover, FIG. 3 shows a set of equipment usable in implementation of the method, FIG. 5 shows a third magnetic particle remover located in a reaction vessel and usable for implementation of the method, and FIG. 6 shows a top view of the remover in FIG. 5

Figure 4:
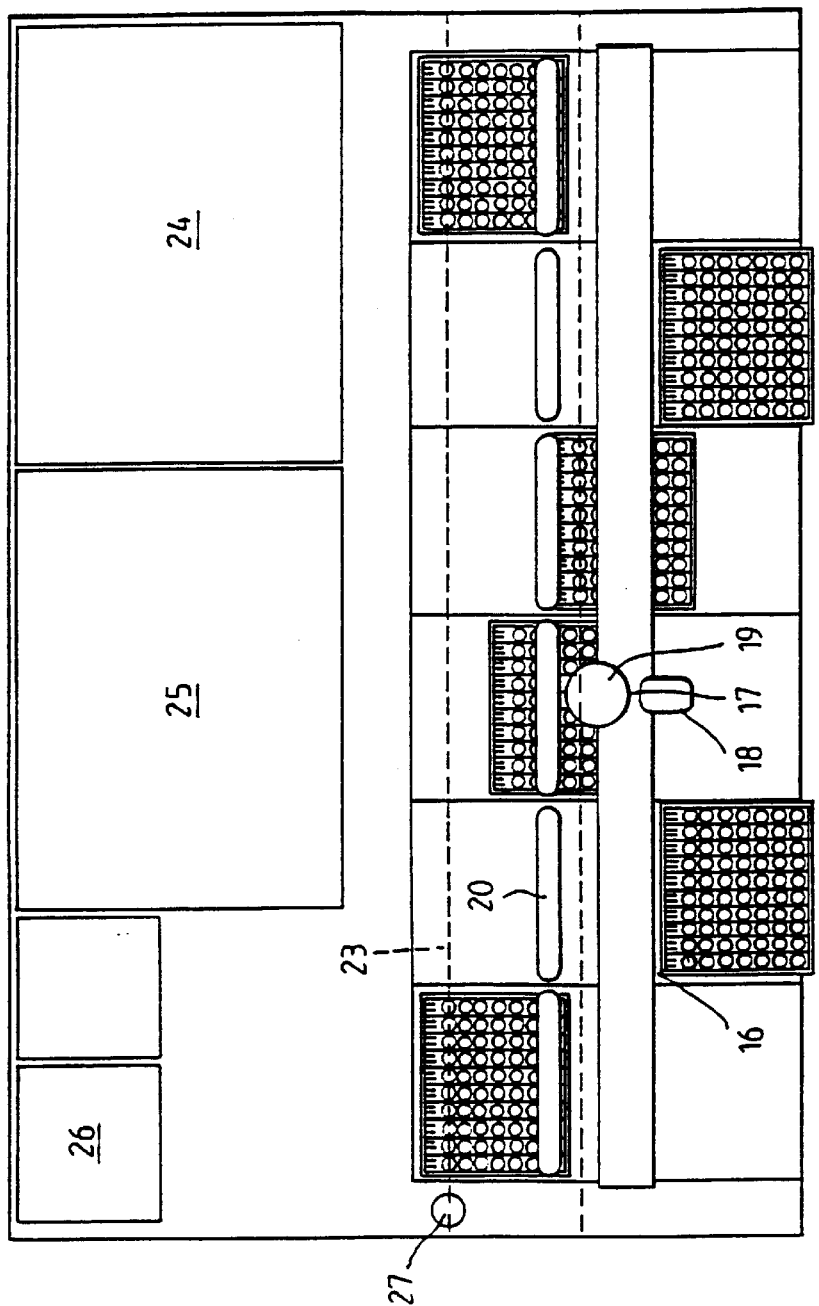
FIG. 4 shows another set of equipment of greater capacity.

In accordance with FIG. 1, immunodetermination is performed by using a plate 1, which consists of wells 2 located in a straight line and a remover 3 provided with a cylindrical sheath 4. At its bottom end the remover has a sharp point 5 and the bottom end is shaped as a cone 6. At its top end the remover has a handle 7 which is advantageous for robotics and at which the remover can be grasped for exact control of its horizontal and vertical positions. The well also contains magnetic particles 8 coated with a separating reagent which reacts to form a complex with the analyte to be determined. The remover has a bore 9 containing a movable pin 11 provided with a magnet 10.

The magnet 10 in FIG. 1 has two magnets one above the other so that identical poles are opposite to one another (SN-NS). In this way a powerful change of the magnetic field is created at the junction of the magnets and also an advantageous situation for pulling the particles to this point on the remover 3 surface. Correspondingly, the outside field of the magnet couple weakens in the vertical direction, whereby particles will gather more easily only at the location of the magnets. Several magnets can be placed similarly after each other. This is advantageous when a narrow structure is desired.

The sample to be examined is brought first to the first well 2 in plate 1 containing a suitable diluter, if required, whereupon magnetic particles 8 coated with the desired separating reagent and a remover 3 are brought into it. At this stage pin 11 is in the upper position, so the particles are moving freely in the well. The analyte possibly contained in the sample is now allowed to react with the separating reagent to form an immunocomplex. During the reaction the remover is moved in the well to promote blending. After incubation the magnet is moved to the lower position, whereby the particles will gather onto the remover surface and they can be moved to the second well. In the second well the particles can again be released, for example, to perform washing or a tracer reaction, and they can then be reassembled and then moved forward. Finally, the measurement required for the determination is performed in the last well.

During reactions and washes the remover 3 is moved back and forth in well 2, whereby the medium will blend effectively.

Plate 1 can be made of some suitable plastic material.

No liquid transfers are required during the determination, whereby a safe, simple and reliably-operating system can be constructed.

The cover 4 diameter is chosen to match the well 2 diameter so that an efficient flow is achieved around the cover when lifting or lowering the cover. When separating particles, several movements back and forth are preferably done with the cover in the well (for example, about 20 times in 10 seconds) with particles adhered to the cover. Weakly adhered particles will then drop off, but then they will probably adhere better.

FIGS. 2a and 2b show implementation of the method by using a remover of another design.

The first well 2 in plate 1 contains magnetic microparticles 8 coated with a separating reagent for the analyte to be determined, and a diluter, if required.

Remover 3.1 has a boring 9 from the top which can receive pin 11 which has a magnet 10 at its lower end. At its lower end the remover has a drop-like extension 12 and its point has a sharp cusp 5. In addition, an annular recess 13 is provided in the extension surface close to its lower end.

The sample is brought to the first well 2, whereafter remover 3.1 is pushed into it with pin 11 in the upper position. When the remover is moved, the medium and particles 8 will blend effectively to form a suspension. Upon completion of the incubation the pin is pushed down, whereby the particles will gather onto the extension 12 surface pulled by magnet 10 and form a dense mass in recess 13 (see FIG. 2b). The remover is now moved to the next well and the pin is pulled up, whereby the particles will again blend with the medium. The particles are taken to the second well containing a first washing fluid, to the third well containing a second washing fluid and to the fourth well containing an enzyme conjugate adhering to the immunocomplex. After tracer incubation the remover is taken through three more reaction and washing wells for measurement in the last well containing an enzyme substrate, from which the enzyme removes a fluorometrically detectable compound. After the substrate reaction, the remover is moved aside and a fluorometric measurement is performed in such a way that both excitation radiation and emission radiation are led through the well mouth.

Light need not be led through the well wall in the determination. For this reason, as cheap a material and as simple a manufacturing technology as possible may be used. To reduce background radiation, the material is preferably opaque.

Luminometric determinations can be carried out in a similar manner.

If the reaction result is measured absorptiometrically, the measuring vessel must be transparent or the radiation must be obtained by a special arrangement (for example, a reflecting bottom) from the measuring vessel to the detector.

FIG. 3 shows a set of equipment where ten determinations may be performed at the same time.

Determination plates 1 are located in cassette 14. At the end of the last well in each plate there is a code 15 telling the equipment about the determination in question. In addition, the code may be used to give other data, especially the ageing time.

Cassette 14 is pushed into the equipment in the longitudinal direction of the plates with the code end first through opening 16, whereupon the cassette will be moved automatically. In the plate crosswise direction the equipment has a movable detector head 17 provided with an identifying device 18 for reading the code and a measuring device 19 for establishing the reaction result. Removers and puncturing units for the well closing films, if such are used, and magnet pin moving units, if such are used, are all located on arm 20. The equipment also has a thermostatic heater for keeping the plates at the desired temperature.

A remover for each sample plate is attached to arm 20. Samples are dosed into the first well in plates 1 in cassette 14 and the cassette is pushed inside. It moves to its extreme position, where identifying device 18 reads code 15, whereby the control unit receives the information needed for performing the determination. The removers are lowered into the first wells. After incubation the removers are lifted up, the plate is moved one step forward and the second step is performed. The process goes on in this way from one well to the next and finally measurement is performed in the last well. The determination result for each plate is shown on display 21.

All determinations may be different provided that they can be preformed in the number of wells available in the plate. All wells may not be needed in all determinations, in which case they do not contain any medium.

Such equipment can of course also be used where both the detector head and the removers are mounted on the same arm.

FIG. 4 shows a modular set of equipment where six cassettes can be handled at the same time.

In plates 1 used in this equipment code 15 is located at the end of the first well. Cassettes 14 are preheated in incubator 22 and they are pushed into the equipment with their code end first through feed opening 16. The removers needed for each cassette are located on arms 20 in the places for the corresponding plates.

The equipment has one common detector head 17, which can be moved in a transverse direction and which has an identifying device 18 and a measuring device 19. The identifying device reads code 15 in each plate and the cassette then moves inward to its extreme position, where a sample and possibly also a diluter is dosed into the first well. Dashed line 23 shows the path of movement of the dosing device. The cassette is then moved outward, so that the first well is located under remover arm 20, and the first step is performed. The cassette is then moved step by step inward, until the last well is located at the measuring device.

FIG. 4 shows a schematic view of the power supplying unit 24, control unit 25, sample dosing pump 25, airing and diluter unit 26 and point washing well 27 in the equipment.

Plate 1 in FIG. 5 is closed by film 28, which is punctured by using remover 3.2. At the mouth of wells 2 there is an enlarged part 29 against which the punctured film will rest. In the top surface of the plate there is a gap 30 between the wells. It reveals any leakage points that may exist between the wells and it also prevents liquids from moving from one well to another through such points of leakage.

The boring in remover 3.2 contains a movable pin 11 with a magnet 10 at its lower end.

Remover 3.2 has an extension 12.2 at its lower end. Its lower part is conical with a sharp point 5. In this way, the extension can be used for puncturing film 28 so that magnetic particles 8 are protected in the sheath above the extension. The extension also functions as an efficient agitating piston. The bottom of wells 2 is shaped conically to match the extension.

Edge 31 in extension 12.2 is made sharp to minimize drop adhering. Correspondingly, lower edge 32 of the enlarged part of well 2 is suitably flared out downward to remove any remaining drop from remover 3.2 as this is removed from the well.

The upper end of remover 3.2 is provided with a conical mouth extension 33, which makes it easier to centralize the sheath in well 2. A plug 34 to close the well mouth is located above the mouth extension.

The remover 3.2 surface above extension 12.2 is provided with vertical ridges 35. Magnetic particles 8 are located in grooves 36 between these ridges and are thus protected during transfer. The groove bottoms are shaped suitable flat to facilitate release into the liquid. The protecting ridges may also be threadlike (for example, one thread with two ends).

I claim:

1. A method for determining the presence of an analyte in a sample, the method comprising the steps of:
    a. inserting a sample to be tested into a reaction vessel;
    b. inserting solid magnetic particles coated with separating reagent into said reaction vessel to react with the sample;
    c. removing said particles from said reaction vessel by inserting a magnet-equipped remover into said reacting vessel, wherein said particles adhere to said remover;
    d. inserting the remover containing the particles into a measuring vessel wherein at least one of said reaction and measuring vessels contains a medium and agitating the medium by moving said remover vertically while said particles adhere to said remover to improve adherence of said particles;
    e. measuring the reaction between the separating reagent and the sample; and
    f. determining the presence of the analyte.

2. The method of claim 1 further comprising the steps of: inserting the remover containing the particles into at least a third medium-containing vessel, agitating the medium in said third vessel and removing the particles from said third vessel.

3. The method of claim 1 wherein said steps include equipping said remover with a cover and reciprocating said cover-equipped remover.

4. The method of claim 1 wherein said reaction vessel contains the medium and a substance is attached to the medium in said reaction vessel.

5. The method of claim 4 wherein the sample reacts with the substance forming a reacted substance which binds any substance from the sample which may disturb later determining steps.

6. A method for removing magnetic separating particles from a fluid, comprising:

provinding a magnetic remover and a vessel containing magnetic particles and said fluid, said remover and said vessel shaped and sized such that vertical insertion of said remover into said vessel causes substantial fluid flow vertically between an inner wall of said vessel and said remover, removing said magnetic particles from said vessel by inserting said remover into said vessel, agitating said fluid by moving said remover up and down while said particles adhere to said remover, and raising said remover from said vessel.

7. The method of claim 6 comprising agitation by repeatedly moving said remover up and down about 20 times in 10 seconds.

8. The method of claim 1 or 6 wherein the remover includes a sheath and a magnet insertable therein.

9. The method of claim 8 wherein the sheath and magnet are simultaneously inserted into said vessel.

10. An apparatus for use in determining the presence of an analyte in a sample, the apparatus comprising:

a. a reaction vessel containing a sample to be analyzed and solid magnetic particles coated with a separating reagent, wherein the separating reagent reacts with the sample;

b. a plurality of vessels for performing intermediate steps on the particles after the reaction between the separating reagent and the sample;

c. a measuring vessel for conducting measurements of the reaction between the separating reagent and the sample;

d. a measuring device for measuring the reaction between the separating reagent and the sample in the measuring vessel;

e. a magnet-equipped remover for inserting and moving the particles from one vessel to another, said remover being vertically movable for agitating a medium contained in each of said vessels while said particles adhere to said remover to improve adherence of said particles.

11. The apparatus of claim 10 wherein the remover is equipped with an outer surface.

12. The apparatus of claim 11 wherein said outer surface has a profiled area for making the particles adhere to the remover as a dense mass.

13. The apparatus of claim 11 wherein said outer surface slopes downward.

14. The apparatus of claim 13 wherein said outer surface has a sharp nodule at its lowest point.

15. The apparatus of claim 10 wherein each of said vessels are joined together for form a single vessel unit.

16. The apparatus of claim 10 wherein at least one of said vessels is closed with a penetrable film.

17. The apparatus of claim 16 wherein each said vessel is closed with a penetrable film.

18. The apparatus of claim 16 wherein at least one closed vessel contains an inert gas.

19. An apparatus for use in determining the presence of an analyte in a sample, the apparatus comprising:

a. a reaction vessel containing a sample to be analyzed and solid magnetic particles coated with a separating reagent, wherein the separating reagent reacts with the sample;

b. a plurality of vessels for performing intermediate steps on the particles after the reaction between the separating reagent and the sample;

c. a measuring vessel for conducting measurements of the reaction between the separating reagent and the sample;

d. a measuring device for measuring the reaction between the separating reagent and the sample in the measuring vessel;

e. a remover for inserting, removing and moving the particles from one vessel to another, said remover containing a magnet for making said particles adhere to said remover after the reaction, said remover being equipped with an outer surface, said outer surface having a profiled area for making said particles adhere to said remover as a dense mass, said outer surface sloping downwardly, and said outer surface being a sharp nodule at its lowest point, wherein at least one vessel contains a medium, and said remover being vertically movable for agitating the medium while said particles adhere to said remover to improve adherence of said particles.

20. The apparatus of claim 10 or 19 wherein the remover includes a sheath and a magnet insertable therein.

21. The apparatus of claim 20 wherein the sheath and magnet are simultaneously inserted into said vessel.

* * * * *